United States Patent
Baldini et al.

Patent Number: 5,530,779
Date of Patent: Jun. 25, 1996

[54] METHOD AND APPARATUS FOR THE IMMOBILIZATION OF VITREOUS SUPPORTS AT THE ENDS OF PLASTIC OR GLASS OPTICAL FIBERS FOR THE CONSTRUCTION OF FIBER-OPTIC CHEMICAL SENSOR

[75] Inventors: Francesco Baldini; Susanna Bracci; Franco Cosi; Riccardo Falciai, all of Firenze, Italy

[73] Assignee: Consiglio Nazionale Delle Ricerche, Roma, Italy

[21] Appl. No.: 270,177

[22] Filed: Jul. 1, 1994

[30] Foreign Application Priority Data

Jul. 6, 1993 [IT] Italy ................... FI93A0125

[51] Int. Cl.⁶ .................................................. G02B 6/00
[52] U.S. Cl. ...................... 385/12; 250/227.23; 436/167
[58] Field of Search ................... 385/12; 250/227.23, 250/227.21; 422/82.06, 82.07, 86, 88; 436/167, 172

[56] References Cited

U.S. PATENT DOCUMENTS

| | | | |
|---|---|---|---|
| 4,803,049 | 2/1989 | Hirschfed et al. | 422/58 |
| 5,244,636 | 9/1993 | Walt et al. | 385/12 |
| 5,244,813 | 9/1993 | Walt et al. | 385/12 |
| 5,298,741 | 3/1994 | Walt et al. | 385/12 |

OTHER PUBLICATIONS

A. M. Scheggi & F. Baldini Chemical sensing with optical fibres Int'l. Journal of Optoelectronics 1993, vol. 8, No. 2 pp. 133–156.

F. Baldini & S. Bracci Optical-fibre sensor by silylation techniques Sensors & Actuators B, 11 (1993) pp. 353–360.

*Primary Examiner*—Akm E. Ullah
*Attorney, Agent, or Firm*—McGlew and Tuttle

[57] ABSTRACT

A description is given of a method for the construction of a fiber-optic sensor in which a chromophore is fixed on a support and said support is linked to at least one optical fiber for the transmission and reception of a light signal. According to the invention, the end of the optical fiber (F) is heated and brought to a softening temperature, and the support (S) is immobilized on the optical fiber (F) by partially incorporating it in the softened portion of the optical fiber and subsequently cooling and solidifying the optical fiber.

11 Claims, 1 Drawing Sheet

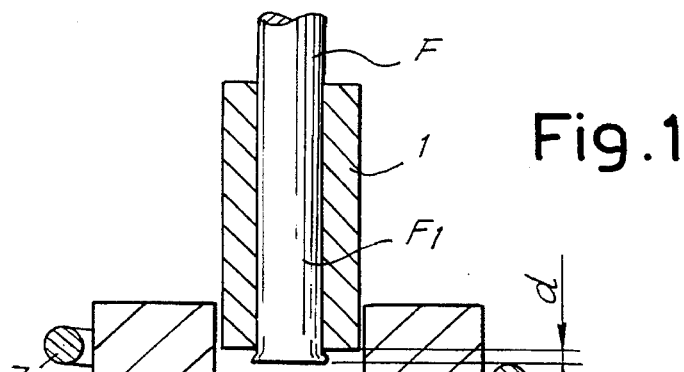
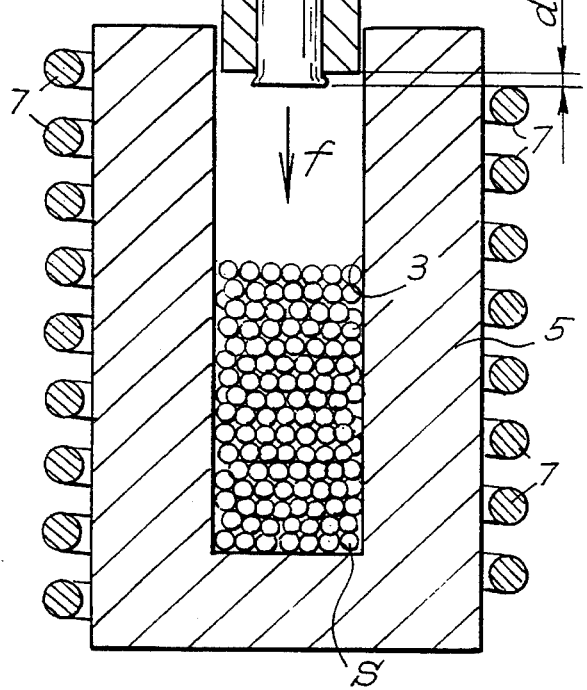
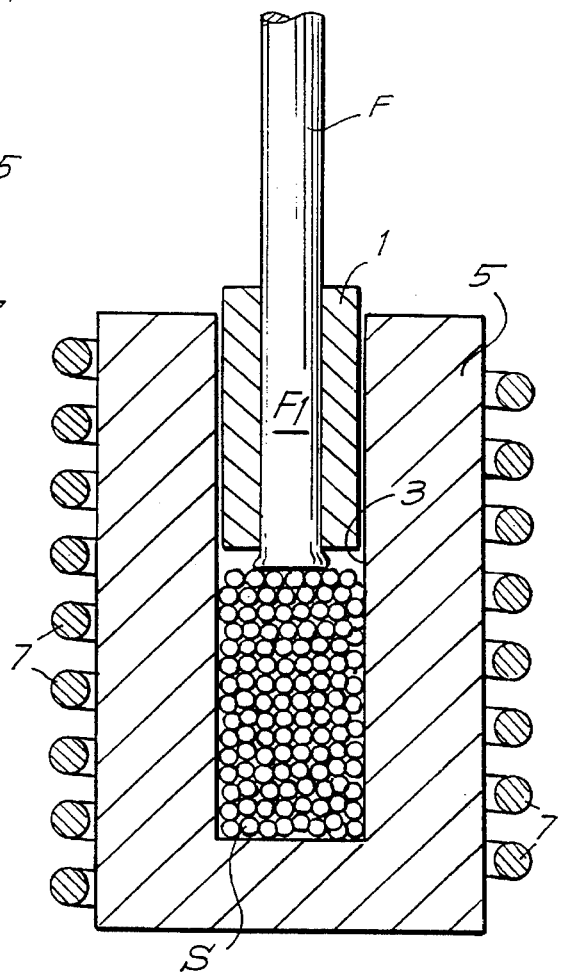
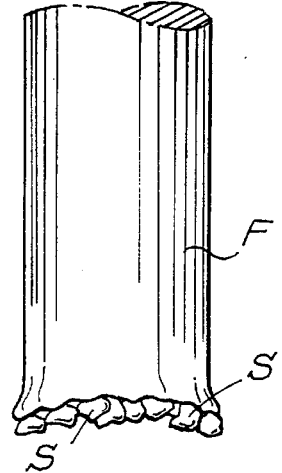

METHOD AND APPARATUS FOR THE IMMOBILIZATION OF VITREOUS SUPPORTS AT THE ENDS OF PLASTIC OR GLASS OPTICAL FIBERS FOR THE CONSTRUCTION OF FIBER-OPTIC CHEMICAL SENSOR

FIELD OF THE INVENTION

The invention relates to a method for constructing a fiber-optic sensor, in which a chromophore is fixed on a support, and the support is linked to at least one optical fiber for the transmission and reception of a beam of electromagnetic waves.

The invention further relates to a fiber-optic sensor comprising at least one optical fiber for transmitting/receiving a beam of electromagnetic waves and, a support to which a chromophore is applied is associated with the end of the optical fiber.

BACKGROUND OF THE INVENTION

In recent times, numerous studies have been performed regarding the construction of chemical sensors making use of optical fibers. Typically, these sensors comprise a system including one or more optical fibers for conducting electromagnetic radiation, especially within the visible range. With these sensors is associated a chromophore, that is to say a substance having electromagnetic radiation absorption characteristics which change as a function of the chemical characteristics of the environment in which the substance is immersed. Sensors of this type are utilized, for example, for taking pH readings.

Currently, these sensors are constructed in accordance with various techniques. One of these techniques involves the application of the chromophore to a polymeric support which is then inserted into a container intended to be applied to the end of the optical fiber. The container is expediently slotted or otherwise made permeable in order to permit penetration by the liquid on which the reading is to be performed. The liquids penetrates within container and thus in contact with the chromophore disposed on the polymeric support. According to another technique, the chromophore is attached directly to the optical fiber rather than to a solid support. This second technique offers numerous advantages, including the high degree of miniaturization, the extremely compact structure, the absence of a probe in which to incorporate the external support and which is fixed to the optical fiber, and reduced response times. Nevertheless, the direct application of the chromophore to the surface of the fiber presents the disadvantage of a low sensitivity of the sensor thus obtained, due to the modest quantity of chromophore which can be immobilized on the fiber. Studies have been carried out on various systems for increasing the quantity of chromophore immobilized on the fibers; among these, it is possible to mention chemical treatments of the surface of the fibers to increase the number of sites available for the formation of the bond with the chromophore, immobilization on the surface of the fiber of a polymer in which the chromophore is incorporated, and the like.

A global view of the various technologies currently known for the construction of chemical sensors making use of optical fibers can be found in A. M. Schggi and F. Baldini "Chemical sensing with optical fibres", International Journal of Optoelectronics, 1993, Vol. 8, No. 2, pages 133–156.

Currently, new technologies are being investigated for fixing the chromophore on new glass-based supports. In F. Baldini and S. Bracci "Optical-fibres sensor by silylation techniques", Sensors and Actuators B, 11 (1993), pages 353–360, a description is for example given of a method for the application of a chromophore to supports made of controlled porosity glass (CPG: controlled-pore glasses): in this case also, a support constituted by the CPG particles, on which the chromophore is immobilized, is subsequently inserted into a cap applied to the terminal end of the optical fibers for conducting the electromagnetic radiation.

SUMMARY AND OBJECTS OF THE INVENTION

The object of the present invention is to propose a simpler and more economic method for the production of fiber-optic sensors, which exhibit high sensitivity.

These and other objects, which will become clear to experts in the art upon reading the text which follows, are achieved in substance by a method wherein the end of the optical fiber intended to constitute the sensor is heated and brought to a softening or partial fusion temperature, and wherein the support for the chromophore is fixed to the optical fiber by partially incorporating it in the softened portion of the fiber and subsequently cooling the optical fiber to solidify again the material constituting said fiber.

It is thus possible to utilize a support having physical and structural characteristics which are suitable for permitting the application of a significant quantity of chromophore to a support. For example, it is possible to utilize CPG particles which are appropriately treated, especially in accordance with the technologies illustrated in the cited article by F. Baldini and S. Bracci. These CPG particles immobilized directly on the end of the fiber permit the availability of a large quantity of chromophore, far greater than that normally immobilizable directly on the optical fiber using conventional technologies.

The application of the chromophore to the support can take place either before or after the immobilization of the support on the end of the fiber. The application of the chromophore after immobilization of the support on the optical fiber is limited only by the need not to impair the optical characteristics of the fiber during the process of application of the chromophore. Conversely, the application of the chromophore after immobilization of the support on the fiber is advantageous in the case of, by way of example, glass fibers, for which it is necessary to provide a heating to high temperature to cause the softening. In this case, the subsequent application of the chromophore avoids the damaging of the latter by reason of the high temperature.

The method according to the invention involves particular advantages when used in combination with plastic optical fibers. Thus, the latter exhibit a low softening temperature, such that the immobilization of the support for the application of the chromophore can take place by very simple means and without special precautions. Nevertheless, it remains possible to apply the method according to the invention to glass optical fibers as well. It is sufficient to be careful to select an optical fiber, the softening point of which is below the softening or melting point of the support to which the chromophore is applied.

The fiber-optic sensor according to the invention is defined in that the support to which the chromophore is applied is immobilized on the end of the optical fiber by means of partial incorporation of the support in the material forming the optical fiber, previously brought to softening temperature.

Further advantageous features of the method of production and of the sensor itself according to the invention are indicated in the appended claims.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIGS. 1 and 2 show two successive phases of the method according to the invention; and FIG. 3 shows the terminal portion of an optical fiber processed according to the method of the present invention.

DETAILED DESCRIPTION OF THE PREFERRED EMBODIMENT

Referring to the accompanying drawing, F indicates an optical fiber, or a plurality of optical fibers, the end F1 of which is inserted into a sleeve 1 of material exhibiting suitable heat resistance. As shown in FIG. 1, the fiber F projects from the front surface of the sleeve 1 by an amount "d" corresponding to the thickness of optical fiber intended to be brought to softening temperature.

The sleeve 1, with its fiber F inserted into it, is inserted in the direction of the arrow f into a chamber 3 of a pot which is generally indicated by 5. Within the chamber 3 there is disposed a certain quantity of the support S which is to be immobilized on the end of the fiber F. The support S is advantageously constituted by particles of controlled porosity glass (CPG), but could be constituted by a different material, still of vitreous type or alternatively of polymeric type, such as a styrene-divinylbenzene copolymer.

This support may have been previously treated to fix the chromophore on it. Around the pot 5 there is disposed a heating means 7, which may be represented by a resistance, by a radio frequency system or some other device suitable for reaching the temperature required for the softening of the fiber F. Clearly, both the heating device 7 and the material of which the pot 5 is made will be selected as a function of the base material constituting the fiber F.

In FIG. 2, the fiber F and the sleeve 1 have been fully inserted within the chamber 3 of the pot in such a manner as to bring the front surface of the fiber F into contact with the support S particles. At this instant, the base material of the fiber F is at a temperature such that this material becomes soft or partially fused. Consequently, a certain quantity of support S particles remains adherent and is partially incorporated in the base material forming the fiber F.

Upon subsequently extracting the fiber and the sleeve 1 from the chamber 3 and allowing the fiber F to cool, the end of the fiber solidifies again, immobilizing particles of support S on the front surface of said fiber, as may be seen in FIG. 3.

It is clear that in the same pot it is possible to treat simultaneously a plurality of optical fibers inserted simultaneously in a single seating or in adjacent seatings of the sleeve 1.

The sensor may be constructed using one or more fibers F on which the support S has been immobilized by the technique which has just been described.

It will be understood that the drawing shows only an exemplification given only as a practical demonstration of the invention, it being possible for this invention to vary in terms of forms and arrangements, without nevertheless departing from the scope of the concept which informs said invention.

We claim:

1. A method for constructing a fiber optic sensor, the method comprising the steps of:

providing an optical fiber;

heating an end of said optical fiber to soften said end of said optical fiber;

placing a support in contact with said softened end of said optical fiber;

cooling said softened end of said optical fiber to solidify said end of said optical fiber and immobilize said support to said solidified end, such that said support is embedded in said end of said optical fiber;

attaching a chromophore to said support.

2. A method in accordance with claim 1, wherein:

said chromophore is attached to said support before said support is immobilized onto said end of said optical fiber.

3. A method in accordance with claim 1, wherein:

said chromophore is attached to said support after said support is immobilized onto said end of said optical fiber.

4. A method in accordance with claim 1, wherein:

said support is formed of controlled porosity glass.

5. A method in accordance with claim 1, wherein:

said optical fiber is formed of plastic.

6. A method in accordance with claim 1, wherein:

said optical fiber is formed of glass.

7. A method in accordance with claim 1, further comprising:

providing a sleeve;

inserting said end of said optical fiber into said sleeve to have said end extend out of said sleeve by an amount of said optical fiber to be attached to said support;

providing a pot containing said support;

inserting said sleeve with said optical fiber into said pot and bringing a front surface of said optical fiber into contact with said support in said pot.

8. A method in accordance with claim 7, further comprising:

heating said pot to soften said end of said optical fiber extending out of said sleeve.

9. A method in accordance with claim 1, wherein:

another optical fiber is provided;

said another optical fiber is inserted into said pot substantially simultaneously with said optical fiber.

10. A method for constructing a fiber optic sensor, the method comprising the steps of:

providing an optical fiber formed of plastic;

heating an end of said optical fiber to soften said end of said optical fiber;

placing said support in contact with said softened end of said optical fiber;

cooling said softened end of said optical fiber to solidify said end of said optical fiber and immobilize said support to said solidified end;

attaching a chromophore to a support.

11. A method for constructing a fiber optic sensor, the method comprising the steps of:

provide an optical fiber;

providing a support to be attached to said optical fiber;

providing a sleeve;

inserting an end of said optical fiber into said sleeve such that said end extends out of said sleeve by an amount of said optical fiber to be attached to said support;

providing a pot containing said support;

inserting said sleeve with said optical fiber into said pot;

heating an end of said optical fiber to soften said end of said optical fiber;

placing said support in contact with said softened end of said optical fiber;

cooling said softened end of said optical fiber to solidify said end of said optical fiber and immobilize said support to said solidified end;

attaching a chromophore to a support.

* * * * *